United States Patent [19]

Udovich

[11] 4,328,120

[45] May 4, 1982

[54] CATALYST FOR THE OXIDATION OF BUTANE TO MALEIC ANHYDRIDE

[75] Inventor: Carl A. Udovich, Joliet, Ill.

[73] Assignee: Standard Oil Company (Indiana), Chicago, Ill.

[21] Appl. No.: 139,233

[22] Filed: Apr. 11, 1980

[51] Int. Cl.³ .................... B01J 23/12; B01J 23/22; B01J 27/18
[52] U.S. Cl. ................................. 252/435; 252/437; 549/260
[58] Field of Search ..................... 252/435, 437; 260/346.75

[56] References Cited

U.S. PATENT DOCUMENTS

| | | | |
|---|---|---|---|
| 4,097,498 | 6/1978 | Barone et al. | 252/435 X |
| 4,151,116 | 4/1979 | McDermott | 252/437 X |
| 4,218,382 | 8/1980 | Milberger et al. | 252/437 X |

*Primary Examiner*—W. J. Shine
*Attorney, Agent, or Firm*—Gunar J. Blumberg; William T. McClain; William H. Magidson

[57] ABSTRACT

A novel catalyst for the oxidation of butane to produce maleic anhydride comprising a phosphorus and vanadium mixed oxide promoted by uranium wherein the catalyst is prepared by using an organic medium and has two specific phases identified by characteristic X-ray pattern. A process for the manufacture of maleic anhydride from butane feedstock utilizing the novel catalyst.

2 Claims, No Drawings

CATALYST FOR THE OXIDATION OF BUTANE TO MALEIC ANHYDRIDE

BACKGROUND OF THE INVENTION

1. Field of the Invention

The field of this invention relates to the production of maleic anhydride from n-butane and catalysts therefor.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known and the principal method currently employed for the manufacture of maleic anhydride is by the air oxidation of benzene in the presence of certain heavy metal oxide catalysts. However, because of the inherent toxicity of benzene fumes, the trend has been to eliminate the utilization of benzene as a feedstock and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411, 3,832,359, 3,888,886, 4,002,650, 4,147,661, 4,149,992, 4,151,116, 4,152,338, 4,152,339 and British Application 2,019,839A. While the aforementioned prior art tends to bring about some improvement in the performance of the phosphorus vanadium catalyst there remains much room for improvement, particularly from the standpoint of high conversion, yield and catalyst life.

The object of the present invention is to provide a phosphorus vanadium uranium oxide catalyst prepared in an organic medium which prior to its use in the manufacture of maleic anhydride from butane feedstock is in a phase comprising in excess of eighty percent of a characteristic powder X-ray diffraction pattern using copper K alpha radiation as follows:

| d angstrom | Line Position 2.θ degrees | Intensity |
|---|---|---|
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 | which when used in the manufacture of maleic anhydride from butane at a temperature of about 700° to 850° F. converts to a second phase having a characteristic powder X-ray diffraction pattern using copper K alpha radiation as follows:

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

A further object is to provide a process for the manufacture of maleic anhydride from butane at a temperature of about 650° to 850° F. in the presence of the novel catalyst.

A catalyst for the production of maleic anhydride by the oxidation of butane which comprises a phosphorus-vanadium mixed oxide with uranium as the promoter, the atomic ratio of vanadium to phosphorus being in the range of 0.5:1 to 1.25:1 and the total atomic ratio of uranium to vanadium being in the range of 0.01:1 to 0.3:1 wherein the catalyst in the initial phase has a characteristic powder X-ray diffraction pattern using K alpha radiation as follows:

| d angstrom | Line Position 2.θ degrees | Intensity |
|---|---|---|
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 | which upon heating at a temperature of about 600° to 800° F. under reaction conditions for the oxidation of butane to maleic anhydride converts to a phase having a characteristic powder X-ray diffraction pattern using copper K alpha radiation as follows:

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

The novel catalyst comprises a phosphorus vanadium mixed oxide promoted by uranium. The atomic ratio of the vanadium to phosphorus can suitably be in the range of 0.5:1.0 to 1.25:1.0 preferably in the range of 0.6:1.0 to 1.0:1.0. The total atomic ratio of uranium too vanadium advantageously is in the range of 0.01:1 to 0.3:1. It is preferred that the total atomic ratio of uranium to vanadium should be in the range of 0.03:1 to 0.25:1. The atomic ratio of phosphorus to vanadium is suitably in the range of 0.8:1 to 2:1, preferably 1:1 to 1.7:1.

Catalysts prepared according to the invention may be made from an organic solvent system wherein vanadium pentoxide in the presence of uranium (IV oxide) is reduced with gaseous hydrogen chloride. Subsequent reaction of the vanadium uranium oxide solution with crystalline orthophosphoric acid and removal of water of reaction by azeotropic distillation results in precipitation of a crystalline vanadium phosphorus uranium mixed oxide which may suitably be filtered from the mother liquor, dried and then employed as an oxidation catalyst for the manufacture of maleic anhydride from butane feedstock. Suitably, organic solvents are alcohols, or mixtures of alcohols, with aromatic hydrocarbons such as benzene, orthoxylene and etc. Aliphatic alcohols are usually employed in the process and isobutanol is the preferred alcohol. The precipitation of the phosphorus vanadium uranium oxide complex is achieved by reducing the solubility of this complex in solution by employing a co-solvent. Precipitation can also be effected by reducing the temperature and removal of the solvent. The use of a co-solvent such as benzene or orthoxylene also functions to facilitate removal of excess water through azeotropic distillation. Precipitation of the phosphorus vanadium uranium oxide mixed oxide can suitably be effected by azeotropic distillation of the organic solvent and the water of reaction and subsequent evaporation of the organic solvent. The uranium may be added as a compound together with vanadium or separately introduced into the solution. Suitable uranium compounds comprise uranium (VI) oxide, uranium (VI) dinitrate, uranium (VI) dichloride, uranium (IV) hydrogen phosphate dioxide, uranium (IV) oxide, uranium (V) oxide, uranium sulfate-dioxide, uranium (VI) acetate and other soluble uranium salts. If it is desired to improve physical properties of the catalysts it may be treated with the suspension of an inert support for example alumina, titania, silicon carbide, kieselguhr, pumice or preferably silicon. The catalyst may be reinforced with such materials at any stage in its preparation.

According to our process, the average valence of vanadium is in the range of about 4.0 to 4.4. In our catalyst preparation, various anhydrous phosphoric acids may be used including ortho-phosphoric, pyrophosphoric, triphosphoric acid or meta-phosphoric acid. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

It has been discovered that the catalyst having a characteristic phase one showing an X-ray diffraction pattern as follows:

| d angstrom | Line Position 2.θ degrees | Intensity |
|---|---|---|
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 | which when utilized in the manufacture of maleic anhydride from butane feedstock at a temperature of about 650° to 850° F. has a second phase having the following X-ray pattern.

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

The aforementioned X-ray forms comprise at least eighty percent of the catalyst. This catalyst shows excellent selectivity and yield in the manufacture of maleic anhydride from butane. Also, this catalyst has a long life and can be regenerated in situ, thus, making it useful for the commercial production of maleic anhydride.

In a preferred embodiment a solution of a vanadium compound in the hydrocarbon solvent is produced by the reduction of vanadium pentoxide with gaseous hydrogen chloride. A uranium compound, preferably an oxide is added to the solution prior to the reduction stage. The temperature at which the vanadium oxide is reduced is in the range of 70° to 230° F. and preferably 90° to 160° F.

After reduction, phosphorus is added suitably as orthophosphoric acid preferably as 100% orthophosphoric acid. After precipitation of the mixed oxide and a suitable digestion period, it is filtered from the mother liquor and dried in a vacuum oven at about 200° to 250° F. under a positive nitrogen bleed. The dried mixed oxide may be activated by heating it in the presence of a hydrocarbon such as n-butane.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen but synthetic manufactures of oxygen and diluent gases such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger type reactors are quite satisfactory. The tops of such reactors may vary in diameter from about one-quarter inch to about three inches, and the length may be varied from about three to about ten or more feet.

The oxidation reaction is an exothermic reaction and, therefore, relatively close control of the reaction temperatures should be maintained. It is desirable to have the surface of the reactors at a relatively constant temperature and some medium to conduct heat from the reactors is necessary to aid temperature control. Such media may be Woods metal, molten sulfur, mercury, molten lead and the like, but it has been found that eutectic salt baths are completely satisfactory. One such bath salt is a sodium nitrate, sodium nitrate-potassium nitrate eutectic constant temperature mixture. An additional method of temperature control is to use a metal block reactor whereby the metals surrounding the tube act as a temperature regulating body. As will be recognized by a man skilled in the art, the heat exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a present heat zone under an inert material such as one-quarter inch Alundum pellets, inert ceramic balls, nickel balls, or chips and the like present at about one-half to one-tenth the volume of the active catalyst present.

The temperature of the reaction may be varied within some limits but, normally the reaction should be conducted at a temperature within a rather critical range. The oxidation reaction is exothermic and once reaction is underway, the main purpose of the salt bath or other media is to conduct heat away from the balls of the reactor and control the reaction. Better operations are normally obtained when the reaction temperature employed is no greater than 20°-50° F. above the salt bath temperature. The temperature of the reactor, of course, will also depend to some extent upon the size of the reactor and the butane concentration.

The reaction may be conducted at atmospheric, super atmospheric, or below atmospheric pressure. The exit pressure will be at least slightly higher than the ambient pressure to insure a positive flow from the reaction. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride. The following examples will serve to provide a fuller understanding of the invention, but it is to be understood that these examples are given for illustrative purposes only and will not be interpreted as limiting the invention in any way. In the examples the terms "conversion", "selectivity" and "yield" are defined as follows:

Conversion % = $\frac{\text{Moles hydrocarbon reacted}}{\text{Moles hydrocarbon in feed}} \times 100$ Selectivity % = $\frac{\text{Moles maleic formed}}{\text{Moles hydrocarbon consumed}} \times 100$ Yield Wt. % = (Conversion) × (Selectivity) × 1.69

EXAMPLE 1

To a 2 liter 4-neck flask equipped with mechanical strirrer, reflux condenser, thermometer, barrett trap, and submersible gas inlet tube are charged 500 ml isobutanol, 27 g (0.1 gfw) uranium (IV) oxide and 91 g (0.5 gfw) vanadium pentoxide. Gaseous $HCl_{(g)}$ is introduced at such a rate as to control the exotherm at 70° C. The reduction proceeds smoothly and the solution becomes homogeneous red-brown without suspended solids of $V_2O_5$.

After reduction is complete, the solution is cooled to 50° C. and 125 g of crystalline orthophosphoric acid is added along with 250 ml of benzene. The solution is brought to reflux and allowed to reflux overnight with periodic removal of water-azeotrope (65 ml). The suspended solids are filtered and washed with isobutanol to a clear wash. The catalyst (130 g) is dried under vacuum with a nitrogen bleed overnight.

A sample of this mixed oxide is analyzed by X-ray and gives the following results:

| d angstrom | Line Position 2.θ degrees | Intensity |
|---|---|---|
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 |

EXAMPLE 2

The mixed oxide prepared in example 1 is combined with 5% sterotex and formed into ⅛" pills for catalyst evaluation. A 4 g loading of catalyst is placed in an evaluation mini-reactor under a water saturated (23° C.) 1.05% butane-synthetic air mixture stream and heated to 250°-300° F. for 2 hrs. to remove sterotex. The mixed oxide is brought to 760° F. over the next 4 hours and analysis for maleic anhydride is done by gas liquid partition chromotography. Results are as follows:

| Time on Stream (hrs.) | Conversion (butane) | Selectivity (maleic) | Yield (maleic) | Temp. (°F.) |
|---|---|---|---|---|
| 24 | 75 | 67 | 85 | 763 |
| 168 | 75 | 68 | 86 | 777 |
| 216 | 77 | 67 | 87 | 790 |

A sample of the activated catalyst is submitted to X-ray analysis and the following results are obtained:

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

I claim:

1. A catalyst for the production of maleic anhydride by the oxidation of butane which consists essentially of a phosphorus-vanadium mixed oxide with uranium as the promoter, wherein vanadium pentoxide in the presence of uranium is reduced and subsequently the vanadium uranium oxide solution is reacted with phosphoric acid, the atomic ratio of vanadium to phosphorus being in the range of 0.5:1 to 1.25:1 and the total atomic ratio of uranium to vanadium being in the range of 0.1:1 to 0.3:1 wherein the catalyst in the initial phase has a characteristic powder X-ray diffraction pattern using copper K alpha radiation as follows:

| d angstrom | Line Position 2.θ degrees | Intensity |
|---|---|---|
| 5.7 | 15.6 | 67 |
| 4.5 | 19.7 | 47 |
| 3.7 | 24.3 | 36 |
| 3.3 | 27.1 | 53 |
| 3.1 | 28.8 | 26 |
| 2.9 | 30.5 | 100 |
| 2.8 | 32.2 | 17 |
| 2.7 | 33.7 | 20 | which upon heating at a temperature of about 600° to 800° F. under reaction conditions for the oxidation of butane to maleic anhydride converts to a phase having a characteristic powder X-ray diffraction pattern using copper K alpha radiation as follows:

| d angstrom | Line Position 2.θ degrees | Intensity |
|---|---|---|
| 6.3 | 14.2 | 10 |
| 4.8 | 18.5 | 7 |
| 3.9 | 23.0 | 100 |
| 3.1 | 28.5 | 58 |
| 3.0 | 30.0 | 29 |
| 2.7 | 33.8 | 7 |

2. The catalyst of claim 1, wherein there are 0.8:1 to 2:1 atoms of phosphorus present for each atom of vanadium.

* * * * *